United States Patent

Skelton et al.

(10) Patent No.: US 8,715,704 B2
(45) Date of Patent: May 6, 2014

(54) LURE

(75) Inventors: Amanda Skelton, London (GB); Mary Cameron, London (GB); Michael Alexander Birkett, Hertfordshire (GB); John Anthony Pickett, Hertfordshire (GB)

(73) Assignees: London School of Hygiene & Tropical Medicine, London (GB); Rothamsted Research Limited, Hertfordshire (GB)

(*) Notice: Subject to any disclaimer, the term of this patent is extended or adjusted under 35 U.S.C. 154(b) by 223 days.

(21) Appl. No.: 12/812,075

(22) PCT Filed: Jan. 19, 2009

(86) PCT No.: PCT/GB2009/000140
§ 371 (c)(1),
(2), (4) Date: Aug. 19, 2010

(87) PCT Pub. No.: WO2009/090412
PCT Pub. Date: Jul. 23, 2009

(65) Prior Publication Data
US 2010/0310499 A1    Dec. 9, 2010

(30) Foreign Application Priority Data

Jan. 17, 2008   (GB) .................................. 0800894.8
Feb. 12, 2008   (GB) .................................. 0802580.1

(51) Int. Cl.
*A01N 25/00*   (2006.01)

(52) U.S. Cl.
USPC ........... 424/421; 424/405; 424/406; 424/409; 424/417; 424/764; 514/65; 514/72; 514/529; 514/764

(58) Field of Classification Search
None
See application file for complete search history.

(56) References Cited

U.S. PATENT DOCUMENTS

2003/0091657 A1* 5/2003 Chiasson ..................... 424/725

FOREIGN PATENT DOCUMENTS

JP          52-041226       *  3/1977
WO     WO 03/051112 A1     6/2003

OTHER PUBLICATIONS

Nagai et al *Acarus* mite-repellent tool—abstact # 129:299246 of JP 10259102.*
U Nagai et al *Acarus* mite-repellent tool—abstact # 129:299246 of J P 10259102 ;Sep. 1998.*
Ruther and Steidle, "Mites as Matchmakers: Semiochemicals from Host-Associated Mites Attract Both Sexes of the Parasitoid *Lariophagus distinguendus*," *J Chem. Ecol.* 26:1205-1217, 2000.

* cited by examiner

*Primary Examiner* — Neil Levy
(74) *Attorney, Agent, or Firm* — Klarquist Sparkman, LLP

(57) ABSTRACT

The invention relates to a lure for attracting, and in some circumstances, killing dust mites, especially house dust mites. The lure comprises neryl formate and/or limonene and is usually arranged in powder form to allow it to be shaken over an area containing the mites. What about liquid that dries.

17 Claims, 2 Drawing Sheets

LURE

CROSS REFERENCE TO RELATED APPLICATIONS

Figure 1:
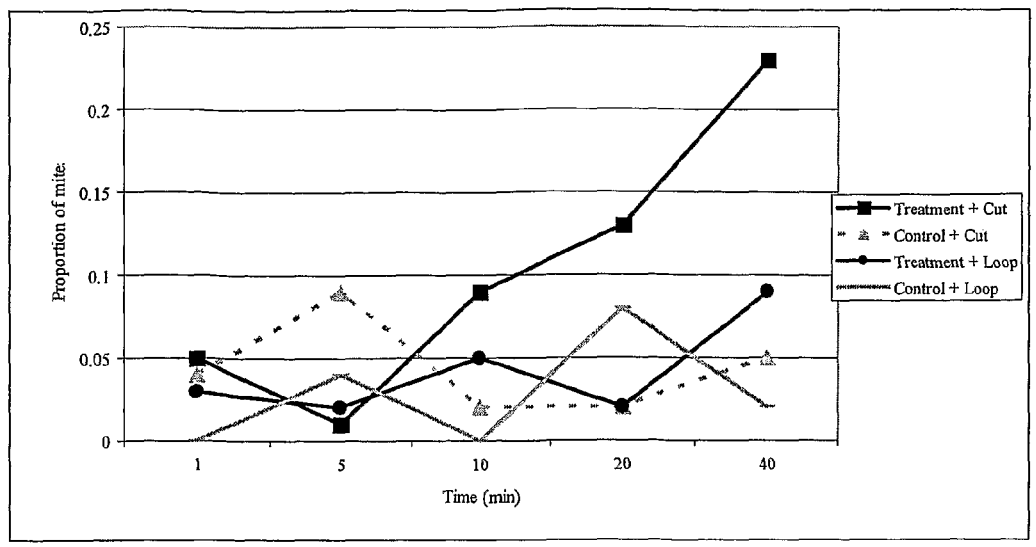

This is the U.S. National Stage of International Application No. PCT/GB2009/000140 filed Jan. 19, 2009, which was published in English under PCT Article 21(2), which in turn claims the benefit of Great Britain Application No. 0800894.8, filed Jan. 17, 2008, and Great Britain Application No. 0802580.1, filed Feb. 12, 2008.

The invention relates to compositions useful in trapping house dust mites.

Atopic diseases such as asthma, which are associated with allergens, are a growing public health problem, with the current economic cost of asthma in the UK being estimated in the region of UK £1.05 billion (WHO, 2006). *Dermatophagoides pteronyssinus* (Trouessart) (European house dust mite) and *D. farinae* (Hughes) (American house dust mite) are found throughout the developed world (Fain et al., 1990; Hart, 1995; Arlian and Morgan 2003), and are known to excrete allergens that cause atopic diseases (Voorhorst et al., 1964; Tovey et al., 1981; Robinson et al., 1997). A worldwide study concluded that there was a high prevalence of asthma in the UK, as well as other developed countries such as Australia, New Zealand and USA (ISSAC, 1998).

There are many different approaches to controlling and reducing house dust mite populations: environmentally, by manipulation of habitat conditions, the direct application of chemicals that act by toxic modes of action, allergen removal, and the use of physical barriers such as impermeable bed covers. Relative humidity is known to affect the house dust mite life cycle (Colloff, 1987; Arlian, 1992; Oribe and Miyazaki, 2000). Therefore, by reducing humidity to less than 51%, experimental trials have shown significant reductions in mite and allergen levels (Arlian et al., 2001). Recently, there have been developments on using hygrothermal models to control *D. pteronyssinus* populations (Crowther et al., 2006). Other environmental methods which have undergone experimental trials in an attempt to reduce mite populations include the use of sub-floor heating (de Boer, 2003), steam cleaning (Colloff et al., 1995), washing clothes and bed linen above 55° C. (McDonald and Tovey, 1992), and freezing soft toys (Nagakura et al., 1996). Synthetic chemical acaricides such as benzyl benzoate and pyrethroids (permethrin and δ-phenothrin), found in commercially available products, can also be used to control house dust mites by applying them to house dust mite habitats (carpets, mattresses, soft furnishings) (Colloff, 1990; Fain et al., 1990; Chang et al., 1996; Heide et al., 1997). Permethrin can also be impregnated on to mattress-liners, and a clinical trial demonstrated success at controlling house dust mites for at least 27 months (Cameron and Hill, 2002). Regular vacuum cleaning can reduce the allergen reservoir on beds and carpets, with vacuuming at weekly intervals being more effective than monthly vacuuming (Bellanti et al., 2000). Recommended medical vacuums which are fitted with high efficiency particulate air (HEPA)-filtering systems that prevent escape of particles >1 µm in diameter reportedly perform better than conventional vacuum cleaners (Colloff et al., 1995). However, the range of efficacy between the HEPA-filtered vacuum cleaners was considerable, with one model performing no better than a conventional vacuum cleaner (Hill and Cameron, 1999). Wet vacuuming might increase the removal of *D. pteronyssinus* allergen, Der p 1, as it is highly water-soluble, although other mite allergens may be less soluble (Colloff et al., 1995). A current more favourable approach is the use of allergen-impermeable bed covers to reduce exposure to allergen in the bed, but studies have shown mixed clinical benefit. For example, one study found a significant reduction in allergen levels, but with no significant improvement in allergic rhinitis in patients (Terreehorst et al., 2003), whereas another study also found a significant reduction in allergen levels with an improvement in asthma symptoms (van den Bemt et al., 2004). However, Luczynska et al., (2003) found that allergen-impermeable covers failed to either reduce allergen levels or alleviate asthma symptoms.

Although there are many methods of house dust mite control, they are not without their limitations. Environmental control measures have to be regularly maintained, otherwise populations will re-establish. Also, if a domestic household receives more knowledge on environmental control, this does not necessarily mean that these measures will be implemented (Callahan et al., 2003). For chemical control, acaricide treatments need to be regularly applied, otherwise re-colonisation of mites will occur, either due to the lack of ovicidal activity (Colloff et al., 1992), or due to a lack of penetration of treatments deep inside the furniture (de Boer, 1998). Furthermore, many asthmatic patients are reluctant to use these products, especially in dormitory areas (Colloff, 1990). Vacuuming needs to occur regularly, and vacuum cleaners cause problems as they can release house dust mite allergen into the air from the vacuum (Kalra et al., 1990). Clinical trials have shown a range of efficacy in using impermeable bed-covers to alleviate symptoms of atopic disease and some patients may find them uncomfortable. Finally, a problem applicable to all control measures is the recruitment of house dust mites from external factors such as dogs (Jackson et al., 2005), car seats (Arlian and Morgan, 2003), hospitals (Custovic et al., 1998) and passenger trains (Uehara et al., 2000).

With current methods exhausted, alternative methods are being studied and tested. For example, incorporating a lure into a house dust mite control method could have the potential to draw mites from deep inside the furniture and mattresses, where upon they would become exposed to a naturally produced acaricide and subsequently vacuumed. Semiochemicals (behaviour-modifying chemicals) have the potential to be used to manipulate house dust mite behaviour, and offer a natural, alternative method to controlling these medically important arthropods. However, the chemical ecology of house dust mites has received little attention, with limited success. Studies have included identifying the chemical profiles of *D. farinae* and *D. pteronyssinus* (Kuwahara et al., 1990; Kuwahara, 1997; Kuwahara, 2004), the identification of the sex pheromone of *D. farinae* (Tatami et al., 2001), and observations on aggregation behaviour but with no chemical identified for evoking the behaviour (Reka et al., 1992; Glass et al., 2001). The inventor has identified house dust mite semiochemicals, and developed a lure-and-kill strategy for mite control.

According to the invention there is provided a composition for luring house dust mites, comprising neryl formate, wherein the composition is in powder form. Alternatively, the composition may be a liquid which forms a powder when it dries.

Also, there is provided a composition for luring house dust mites, comprising limonene, wherein the limonene is substantially in the form of the R-(+)-limonene enantiomer.

Such compositions may comprise both neryl formate and limonene.

The mite may be any mite, especially a house dust mite or a storage mite.

A house dust mite is an arthropod pest commonly found in the carpets and upholstery of human dwellings. As used herein, the term describes any house dust mite, but particularly refers to *Dermatophagoides pteronyssinus*, the European house dust mite, and *Dermatophagoides farinae*, the American house dust mite.

A storage mite is also an arthropod pest, usually found in stored grains and mouldy environments.

Neryl formate is a semiochemical obtained from house dust mites. It is also known as (Z)-3,7-dimethyl-2,6-octadienyl formate and has the following formula:

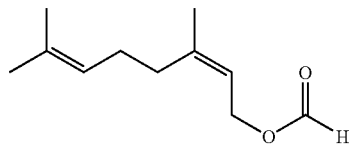

Limonene is a chiral molecule with two enantiomers R-(+)-limonene and S-(−)-limonene. Racemic limonene (equal amounts of both enantiomers) is known as dipentene. Limonene is a terpene and is well known in the art. The limonene in the composition is preferably substantially in the form of the R-(+)-enantiomer, in other words, preferably at least 65% of the limonene is in the form of the R-(+)-enantiomer, more preferably at least 75%, even more preferably at least 85%, more preferably at least 95%. Most preferably, the composition does not contain S-(−)-limonene. Where the term limonene is used in this specification, it is preferably used to refer to the R-(+)-enantiomer.

The composition is preferably in powder form. This allows it to be easily dusted or shaken over a carpet or item of furniture that may contain dust mites. The dust mites are attracted to the composition and are drawn towards the surface of the carpet or piece of furniture, from where they can be more easily removed. Normally dust mites cling to fibres in, for example, carpets, mattresses and pillows and cannot easily be removed. However, by drawing them to the surface, the dust mites can be more easily removed by vacuuming.

It may be preferable in some circumstances for the neryl formate or limonene to be formulated into a powder product which is suitable for sprinkling or dusting. This may be achieved by simple mixing of a small amount of the neryl formate (e.g. a few % w/w) with suitable inert powders, e.g. mineral clay, Fuller's earth, talc, calcium sulphate and/or starch, such that the inert powders do not agglomerate to such an extent as to destroy their sprinkable/dustable properties. Alternatively, the neryl formate may be made into a suspension/emulsion together with an amphipathic carrier (e.g. a modified starch) in an aqueous medium. The suspension/emulsion may then be spray dried, the product of which is a dustable powder containing neryl formate partially or completely encapsulated within the carrier. In many instances, a preferred means of forming a powder formulation is to prepare granules. These may be prepared, for example, by mixing the neryl formate with a diluent powder (e.g. calcium sulphate, calcium phosphate, calcium carbonate, starch or microcrystalline cellulose (all of which are insoluble, and preferred), or e.g. lactose, mannitol, sucrose, sorbitol or dextrose) and a small amount of binder (e.g. an aqueous, alcoholic or hydroalcoholic solution of cornstarch, gelatin, sucrose, acacia, polyvinylpyrrolidone, methylcellulose, sodium carboxymethylcellulose, polyvinyl alcohol or polyethylene glycol) so as to form a moist mass, coarse screening the mass, drying the resulting moist granules, screening the dried granules and optionally mixing with a glidant (e.g. talc, aerated silica or magnesium stearate).

In particular, the composition may be produced in powder form by, for example, formulating the neryl formate and/or limonene into a wax and then into particles. In particular it may be formulated into silicate particles.

In an alternative formulation, the composition may be in the form of a liquid, especially a solution that is arranged to form a powder when it dries. In particular, the composition may be provided in container provided with a nozzle, such as a misting or aerosol nozzle, through which the composition may be driven. The composition may be driven through the nozzle by a pump or any other appropriate means.

The composition may further comprise a compound that is toxic to house dust mites, such as an acaricide. An acaricide is an agent used to kill mites. As used herein, the term includes any type of acaricide, such as natural pyrethroids and essential oils. One particular acaricide that may be used is pyrethrum. The use of other acaricides are also envisaged, especially plant based acaricides.

Also provided by the invention is a composition for luring and killing mites comprising neryl formate and/or limonene and an acaricide.

The composition may be in powder or other form. It may additionally comprise appropriate carriers.

The compositions of the invention preferably comprise neryl formate and limonene, especially the R-(+)-enantiomer of limonene.

The compositions according to the invention preferably comprise neryl formate and/or limonene and/or an acaricide in effective amounts. That is to say, the compositions preferably comprise sufficient neryl formate and/or limonene to lure dust mites to the surface of the material to which the composition is to be applied. The compositions preferably comprise sufficient acaricide to kill at least 50% of the dust mites lured to the surface. The compositions preferably comprise at least 0.01% neryl formate, more preferably at least 0.05%, more preferably at least 0.5%, even more preferably at least 1%.

The compositions may also comprise one or more other mite semiochemicals, especially one or more other attractants.

The invention further provides the use of neryl formate and/or limonene as a lure or an attractant for house dust mites.

A lure or attractant for house dust mites is a composition that attracts house dust mites to it.

Also provided is the use of neryl formate and/or limonene and an acaricide to produce a lure-and-kill composition for house dust mites. A lure-and-kill composition is a composition that attracts house dust mites to it and then kills them. The term lure-and-kill is well known in the art.

Further provided is a method of luring house dust mites comprising exposing the house dust mites to neryl formate and/or limonene.

The term exposing house dust mites to neryl formate and/or limonene preferably means placing neryl formate and/or limonene near to house dust mites. In particular, the neryl formate and/or limonene may be placed within 5 cm of the mites, more preferably within 4 cm of the mite, even more preferably within 3 cm of the mites.

The method may additionally include the step of exposing the house dust mites to an acaricide. Preferably the house dust mites are exposed to the acaricide simultaneously or subsequently to exposure to the neryl formate and/or limonene.

Figure 2:
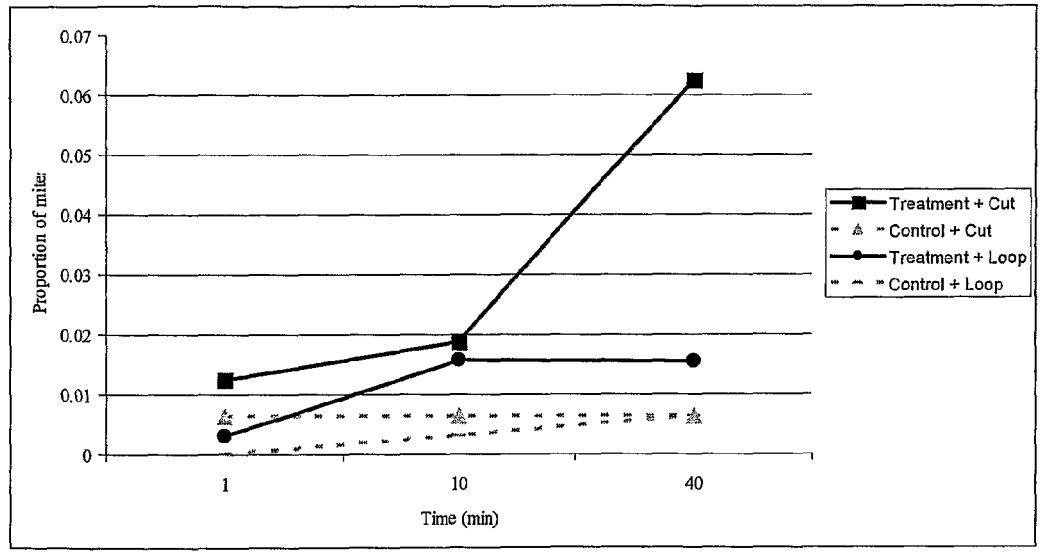
Figure 3:
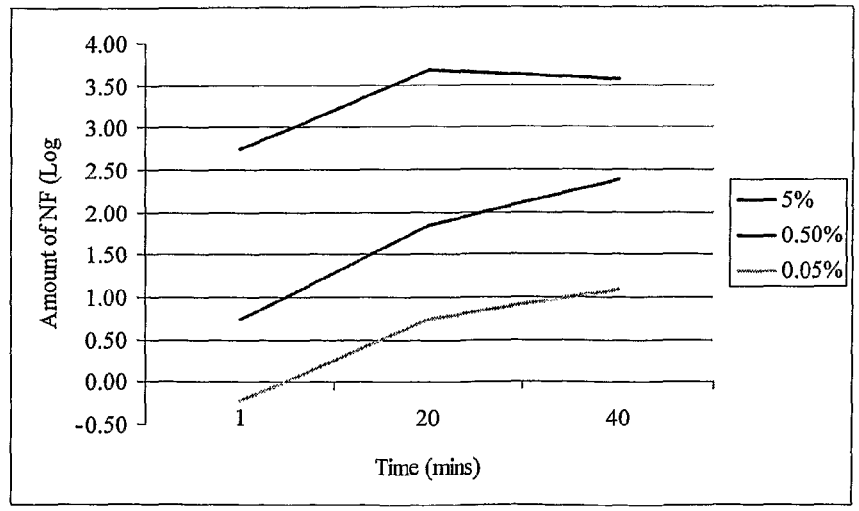
Figure 4:
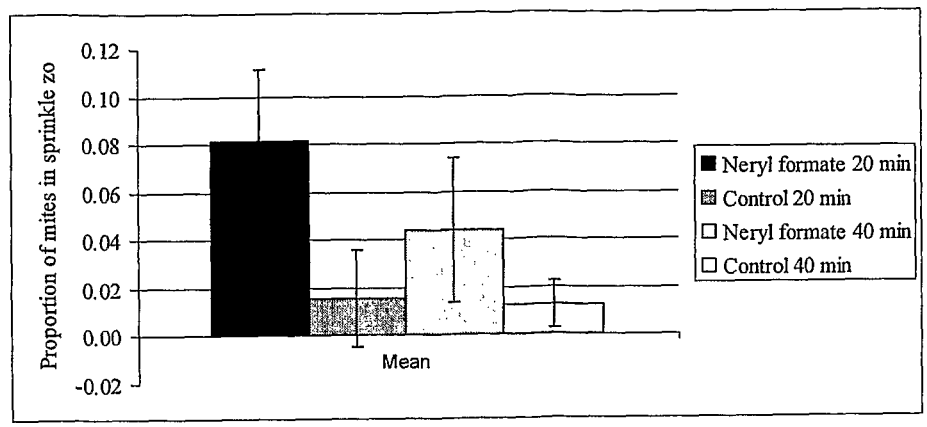
Figure 5:
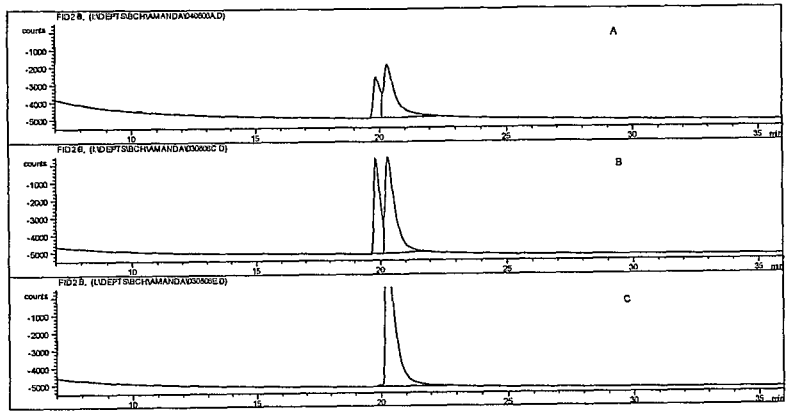
Figure 6:
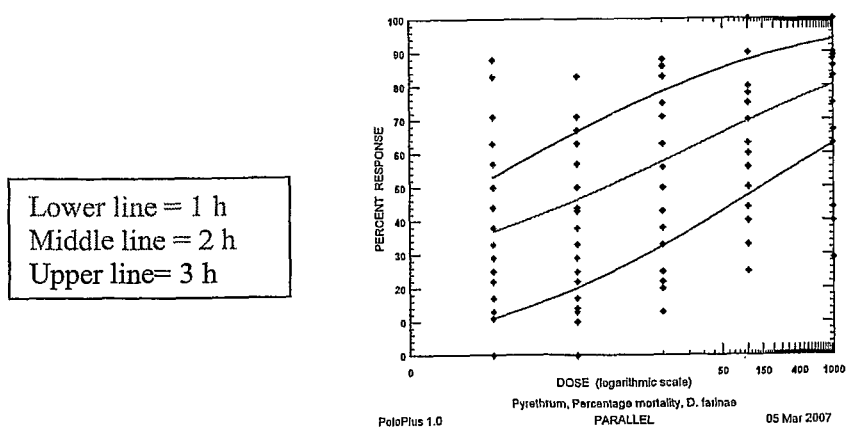

The invention will now be described in detail, by way of example only, with reference to the following drawings:

FIG. 1: Proportion of *Dermatophagoides farinae* mites caught in the lure area (20 mm centre of carpet disc) over time;

FIG. 2: Proportion of *Dermatophagoides pteronyssinus* mites caught in the lure area (20 mm centre of carpet disc) over time;

FIG. 3: Release rates for the three formulations;

FIG. 4: Total Number of *Dermatophagoides farinae* retrieved in "sprinkle zone" after exposure to 0.05% neryl formate formulation;

FIG. 5: GC traces of A) (R)-limonene+*D. pteronyssinus*, B) racemic limonene and C) (R)-limonene; and FIG. 6: Percentage Mortality Data for *Dermatophagoides farinae* after exposure to pyrethrum

EXAMPLE 1

Neryl Formate

Methods and Materials
House Dust Mites.

*Dermatophagoides farinae* were reared as previously reported (Skelton et al., 2007). *Dermatophagoides pteronyssinus* mites were fed on a mixture of ground yeast cells (Allison) and fish flakes (TetraMin), at 23-25° C. and 70-75% relative humidity (Spieksma, 1967; Arlian et al., 1990) and maintained under these conditions until required for behavioural bioassays and chemical analysis.

Preparation of House Dust Mite Extracts.

*Dermatophagoides farinae* and *D. pteronyssinus* cultures (0.1 g) were placed separately at the top of glass measuring cylinders (100 ml) containing saturated NaCl solution (80 ml) (Hart and Fain, 1987; Fain and Hart, 1986). After 10-15 min, mites that remained floating were pipetted into a glass vial. Distilled hexane (10 ml) was added and then left at 4° C. overnight. The solvent layer of each extract was removed into a clean vial, and dried using anhydrous magnesium sulphate. The extract was filtered and concentrated under a gentle stream of nitrogen to a volume of either 50 or 100 µl. The *D. farinae* extract was fractionated by liquid chromatography over Florisil® (60-100 mesh, Aldrich Chemical Company, Gillingham, UK), using distilled hexane (100%), hexane: diethyl ether (5, 10, 20, 50%), diethyl ether (100%) and dichloromethane (100%) as eluants.

Collection of House Dust Mite Volatiles.

*Dermatophagoides farinae* and pteronyssinus mites were transferred from a Petri dish into the PTFE tube using a glass pipette tip and gentle suction. Silanized glass wool was compacted at both ends of the PTFE tube and attached to Tenax TA tubes, at one end, and sealed using Swagelok connectors at the other. A control was carried out simultaneously with another PTFE tube compacted with glass wool and either left empty or containing fish flakes. A positive humidified air-flow was introduced into the PTFE tubes at 100 ml/min, through a charcoal filter to reduce contamination, whilst a negative air-flow was drawn through the PTFE tubes simultaneously at 100 ml/min to indicate the air speed through the PTFE tubes. The air entrainment lasted for 24 h after which the Tenax TA tubes were removed.

Gas Chromatography (GC).

Mite extracts and chromatography fractions were analysed using a Hewlett Packard 6890 GC equipped with a cross-linked methyl silicone capillary column (50 m, 0.32 mm i.d, 0.52 µm film thickness) fitted with a cool-on-column injector and a flame ionization detector (FID). The GC oven was programmed to heat from 30° C. to 230° C. at 10° C./min, and held at 230° C. for 30 min. The carrier gas was hydrogen.

Tenax TA samples were analysed on a Hewlett Packard 6890 GC machine, equipped with a cross-linked methyl silicone capillary column (50 m, 0.32 mm i.d, 0.82 µm film thickness) and a FID. Thermal desorption occurred inside the programmed temperature vaporisation unit (PTV), which was programmed to heat rapidly from 30° C. to 220° C. (16° C./sec). The GC oven was then maintained at 30° C. for 30 sec, and then programmed at 5° C./min increments to 120° C., followed by 10° C./min to 240° C. The carrier gas was hydrogen.

Gas Chromatography-Mass Spectrometry (GC-MS).

Mite extracts and fractions were analysed using a VG AutoSpec mass spectrometer (Fisons Instruments, Manchester, UK), coupled to a Hewlett Packard 5890 GC equipped with a cool-on-column injector. Ionization was by electron impact (70 eV, 250° C.). The GC oven was programmed to heat at 30° C. for 5 min and then 5° C./min until 250° C. The carrier gas was helium. Tentative identifications of mite-specific peaks were based upon comparison of acquired mass spectra with current MS databases (NIST, 2005) or with MS data published in the literature. Identifications were confirmed by peak enhancement with authentic samples (Pickett, 1990).

Synthesis and Quantification of Neryl Formate.

Neryl formate was synthesized in one step from commercially available nerol (>97% purity by GC, Aldrich Chemical Company, Gillingham, UK) using formic acid and 1,3-dicyclohexylcarbodiimide. To calculate the amount of neryl formate present in mite extracts, a single point external standard quantification method was used (Alltech Association, 1998) using peak area data from acquired GC traces.

House Dust Mite Behaviour.

A Y-tube olfactometer was used to observe the behavioural responses elicited by house dust mites, as described previously (Skelton et al., in press). For each experiment, a treatment and control stimulus was added (1 µl) to separate filter paper discs (1.5 cm diameter), allowed to dry for 1 min, and placed into each arm of the olfactometer. A power analysis was carried out at 80% power, 95% significance; to calculate appropriate sample sizes to see 40% difference in effect (70% to treatment) (STATA 8.2 software). Therefore, 20 mites which made a choice were recorded for each treatment experiment as well as mites who failed to make a choice. Treatments comprised: (1) chromatography fractions derived from the *D. farinae* extract .v. hexane, (2) neryl formate (10 & 100 ng/µl) .v. hexane, (3) a female *D. farinae* extract .v. neryl formate, (4) a male *D. farinae* extract .v. neryl formate, and (5) a female *D. pteronyssinus* extract .v. neryl formate.

Statistical Analyses.

Categorical data from the Y-tube olfactometer bioassays were tested with a Chi-squared test for goodness of fit, with a Yates correction factor (preference to a particular arm) (Fowler et al., 1998). Time data were log 10-transformed prior to parametric data analysis. A three-way ANOVA (Minitab 11 for Windows) was carried out to analyse if the log time to make a decision in the treatment arm (neryl formate) was affected by the concentration of neryl formate, gender and house dust mite species studied.

Results

Confirmation and Quantification of Neryl Formate.

Coupled GC-MS analysis of the *D. farinae* fractions suggested that neryl formate was found in fraction 4. The identification was confirmed by the co-injection of fraction 4 with an authentic sample of neryl formate on two GC columns of differing polarity. Using a single point external standard quantification method, the amount of neryl formate per *D. farinae* mite was calculated to be 1.32±0.2 ng and 3.3±0.3 ng for males and females respectively. The amount of neryl formate per *D. pteronyssinus* mite was 0.5±0.01 ng and 1.13±0.11 ng for males and females, respectively. Qualitative analysis of the air entrainment samples indicated neryl formate was present in both *Dermatophagoides farinae* and *D. pteronyssinus* extracts.

Behavioural Activity to House Dust Mite Derived Fractions.

The global responses (males and females of *D. farinae*) to the treatment arm were only significant when fraction four was tested ($x^2$=4.05, df=1, P<0.05, n=20). No significant difference was found for the other fractions tested.

House Dust Mite Olfactory Responses to Neryl Formate.

The global responses of males and females of *D. farinae* when exposed to neryl formate at 10 ng ($x^2$=9.025, df=1, P<0.01, n=40) and 100 ng ($x^2$=4.225, df=1, P<0.05, n=40) were significant to neryl formate (FIG. 3). The global responses (males and females of *D. pteronyssinus*) when exposed to neryl formate at 10 ng ($x^2$=11.025, df=1, P<0.01, n=40) and 100 ng ($x^2$=11.025, df=1, P<0.01, n=40) were also significant to the arm containing neryl formate (FIG. 3). However, there were observed variations in the responses between genders. The males of *D. farinae* only demonstrated a significant response to neryl formate at 100 ng ($x^2$=6.05, df=1, P<0.05, n=20) and the females demonstrated a significant response only at 10 ng ($x^2$=6.05, df=1, P<0.05, n=20). Males of *D. pteronyssinus* demonstrated a significant response to neryl formate at 10 ng only ($x^2$=6.05, df=1, P<0.05, n=20), whereas the females of *D. pteronyssinus* demonstrated a significant response to both 10 ng ($x^2$=4.05, df=1, P<0.05, n=20), and 100 ng ($x^2$=8.45, df=1, P<0.01, n=20). There were no significant differences in the log time taken by *D. farinae* and *D. pteronyssinus* to move past the 1 cm mark point along the arm containing neryl formate when analysing concentration (10 ng against 100 ng of neryl formate) (F=2.38, df=1, P=0.125) or gender effects (F=1.60, df=1, P=0.208). However, a significant difference was found between the log time taken by *D. farinae* compared to *D. pteronyssinus* to move past the 1 cm mark point of the arm containing neryl formate (F=10.30, df=1, P<0.02).

House Dust Mite Olfactory Responses to Synthesised Neryl Formate Versus Neryl Formate from a Con-Specific Extract.

For *D. farinae* males, there was no significant difference in the response to synthetic neryl formate or the male *D. farinae* extract containing naturally produced neryl formate ($x^2$=0.10, df=1, P=0.75, n=14). Similarly, for *D. farinae* females there was also no significant difference in the response to either neryl formate or the female *D. farinae* extract ($x^2$=1.38, df=1, P=0.24, n=18) (FIG. 3). The responses by *D. pteronyssinus* females to either synthetic neryl formate or the female *D. pteronyssinus* extract were not significantly different ($x^2$=0.06, df=1, P=0.80, n=16).

Discussion

*Dermatophagoides farinae* did not demonstrate significant behavioural activity to fractions one, two, three, five and six derived from the *D. farinae* extract, but did respond significantly to fraction four. Neryl formate was tentatively identified in fraction four using GC-MS, and confirmed by peak enhancement, using both a HP-1 and DB wax column. Neryl formate has only been previously tentatively identified as a component of both *D. farinae* and *D. pteronyssinus* extracts (Kuwahara et al., 1990; Tatami et al., 2001) as no peak enhancement was carried out. In the current study, neryl formate elicited significant orientated responses by males and females of *D. farinae* and *D. pteronyssinus* at concentrations of 10 ng and 100 ng. Other astigmatic mite aggregation pheromones are active at these concentrations: for example *Caloglyphus polyphyllae* mites significantly respond to β-acaridial at 10 ng (Shimizu et al., 2001) and *Lardoglyphus konoi* significantly responds to (1R,3R,5R,7R) lardolure at 10 ppm (10 ng/µl) (Kuwahara et al., 1991). When synthetic neryl formate was tested for behavioural responses against the con-specific extract containing neryl formate at the same level, neither *D. pteronyssinus* nor *D. farinae* showed a significant preference for either arm. The results confirm that the chemical causing the behaviour observed in the initial fraction experiment was elicited by the presence of neryl formate. Data analysis of the time showed *D. pteronyssinus* and *D. farinae* moved along the arm at significantly different times when exposed to neryl formate, but this does not infer *D. pteronyssinus* walked faster, as the track the mite moved along was not measured.

As both species of house dust mite responded to neryl formate, by definition the chemical is not acting as an aggregation pheromone, however, semiochemicals are known to induce similar behaviour in closely related species. For example, neryl formate and citral evoke the same behavioural response in four species of *Rhizoglyphus* mites (Akiyama et al., 1997). However, the role of neryl formate in house dust mite behaviour remains unclear. *Dermatophagoides farinae* have been observed clustering in the laboratory (Glass et al., 1998; Reka et al., 1992) and both *D. farinae* and *D. pteronyssinus* have been observed clustering together in this study (A. Skelton, personal observation). It has been suggested that the clustering behaviour is initiated by an arrestant-aggregation pheromone in house dust mite faeces, but the study observing this behaviour did not identify the chemical or chemicals involved (Reka et al., 1992). Therefore, the behavioural responses observed to neryl formate, along with the presence of the chemical in house dust mite volatile collections, suggests it may be involved in the clustering behaviour of house dust mites. The ecological benefits of clustering by house dust mites could be to either protect themselves from dehydration, or as a defence mechanism. Mites may cluster together to reduce the surface area that is exposed to the drier environment and subsequently prevent dehydration. There is evidence to suggest that arthropods aggregate to form a "super-organism" to reduce water loss by reducing the surface area of the individual arthropod, and this behaviour has been observed in *Stenotarus rotundus*, the tropical fungus beetle (Yoder et al., 1992). However, males of a *D. farinae* colony have been observed clustering at hydrating conditions (75% RH). Therefore, temperature and humidity may be ruled out as factors instigating the clustering behavioural response, and semiochemicals suggested (Glass et al., 1998). Alternatively, clustering together may serve as a defence mechanism to protect against potential predators, e.g. Cheyletidae mites (Colloff, 1991) and the formation of big clusters of house dust mites in the homes may disorientate the predators at locating an individual mite (Franz et al., 2001). However, neryl formate may play no role in the clustering of mites. The chemical is commonly found in astigmatic mites (Kuwahara, 2004), and was recently discovered as an aggregation pheromone in *Rhizoglyphus setosus* (Kuwahara, 2006). Neryl formate may be involved in house dust mite recognition of a population presence, with subsequent species-specific semiochemical cues used later to locate a mate, e.g. 2-hydroxy-6-methylbenzaldehyde, which initiates mounting behaviour in male *D. farinae* (Tatami et al., 2001).

The lack of behavioural studies on house dust mites, including studies in homes, has contributed to the problem of house dust mite control. However, the current study has identified a means for controlling house dust mite populations, and could ultimately help in alleviating the symptoms associated with atopic diseases.

EXAMPLE 2

Neryl Formate

Development of Semi-Field Bioassay for Testing Semiochemicals

Initially, a bioassay was designed to test the efficacy of neryl formate in attracting populations of the American house dust mite, Dermatophagoides farinae, and the European house dust mite, D. pteronyssinus, from carpet sections. The bioassay involved the placement of D. farinae and D. pteronyssinus onto cut carpet discs (5 cm in diameter) which were placed underneath a glass Petri dish to maintain humidity. Two types of carpet (both obtained from Heuga Home Flooring BV) were tested: cut pile (Simply Soft Aquarius) and loop pile (Working Week Boucle Ink Pad). Aliquots of a 10 ng/10 μl neryl formate solution (in hexane) were used for the lure treatment, whilst hexane alone was used for the control. Both solutions were injected onto filter paper discs (2 cm diameter) and placed into the centre of the carpet discs. After an allocated time interval (1, 5, 10, 20 or 40 min), a sticky trap was placed onto the carpet to capture the mites, and subsequently placed under a microscope to record the amount and position of the mites, to ascertain if the mites had moved from their original position. Data were analysed using a generalized linear model assuming a binomial distribution with a logit link and dispersion parameter equal to 1.0 (see Table 1). The analysis of deviance for both responses was obtained using the MODEL procedure as implemented in GenStat 8.0 (Rothamsted Research).

TABLE 1

Accumulated Analysis of Variance

| Factor | Total Numbers Retrieved | | Target against n | | Target against count | |
|---|---|---|---|---|---|---|
| | D. farinae | D. pteronyssinus | D. farinae | D. pteronyssinus | D. farinae | D. pteronyssinus |
| Carpet | <.001 | <.001 | <.001 | 0.001 | 0.003 | 0.080 |
| Treatment | <.001 | <.001 | <.001 | <.001 | <.001 | 0.022 |
| Time | 0.462 | 0.514 | 0.004 | <.001 | 0.007 | <.001 |
| Carpet. Treatment | 0.053 | 0.942 | 0.039 | 0.673 | 0.086 | 0.550 |
| Carpet. Time | 0.779 | 0.290 | 0.653 | 0.294 | 0.858 | 0.142 |
| Treatment. Time | 0.238 | 0.288 | 0.105 | 0.595 | 0.119 | 0.836 |
| Carpet. Treatment. Time | 0.635 | 0.907 | 0.231 | 0.316 | 0.265 | 0.184 |

Target data corresponds to mites found on the filter paper or in the area where the filter paper was placed. n = 40 number of mites per bioassay. Count = numbers retrieved in bioassay The data suggested that the presence of neryl formate significantly increased the number of mites retrieved on sticky traps, with the lures working more effectively on the cut pile carpet than the loop pile (see FIGS. 1 & 2). The practicality of using a physical trap was assessed after these experiments. Consequently, it was proposed that using neryl formate in a slow-release formulation, which could be shaken on to the carpets to lure the mites to the surface, then subsequently removed by vacuum cleaning, would be more feasible and a user-friendly concept.

Development of a Slow-Release Powder Formulation for Neryl Formate

Neryl formate was formulated into a wax, then into silicate particles (100 μm diameter). Three formulations were developed, at 5%, 0.5% and 0.05%. To determine the release rate for neryl formate from each formulation, small amounts (1 mg) were subjected to air entrainment using TENAX TA as adsorbent. Time interval periods for sampling were 1, 20 and 40 minutes. After the allocated time, TENAX TA tubes were removed, and the trapped volatiles were analysed on a Hewlett Packard 6890 GC, equipped with a cross-linked methyl silicone capillary column (50 m, 0.25 mm i.d, 0.32 μm film thickness) and a FID. The compound was removed from the tube onto the GC column by thermal desorption, using a PTV unit, which was programmed to heat rapidly from 30° C. to 220° C. (16° C./s). The GC oven was maintained at 30° C. for 30 seconds, then programmed to rise at 5° C./min to 120° C., followed by 10° C./min to 240° C. The carrier gas was hydrogen. Release rates for the three formulations are shown below (FIG. 3).

The neryl formate formulation at 0.05% was selected for further work. Twenty and forty minutes were chosen as the two time points to test the formulation, compared against a blank formulation, using the bioassay described above.

TABLE 2

Accumulated Analysis of Variance

| Factor | Total Numbers Retrieved | Numbers in "Sprinkle Zone" |
|---|---|---|
| Treatment | 0.004 | <.001 |
| Time | 0.066 | 0.052 |
| Treatment. Time | 0.966 | 0.557 |

"sprinkle zone" = the area of carpet covered by the powder.

The data suggested that at 20 minutes, significantly more D. farinae mites were retrieved in the sprinkle zone than at 40 minutes (see FIG. 4).

EXAMPLE 3

Limonene

House Dust Mites.

Dermatophagoides pteronyssinus mites were fed on a mixture of ground yeast cells (Allison) and fish flakes (TetraMin), at 23-25° C. and 70-75% relative humidity (Spieksma, 1967; Arlian et al., 1990) and maintained under these conditions until required for behavioural bioassays and chemical analysis.

Preparation of House Dust Mite Extracts.

D. pteronyssinus cultures (0.1 g) were placed separately at the top of glass measuring cylinders (100 ml) containing saturated NaCl solution (80 ml) (Hart and Fain, 1987; Fain and Hart, 1986). After 10-15 min, mites that remained floating were pipetted into a glass vial. Distilled hexane (10 ml) was added and then left at 4° C. overnight. The solvent layer of each extract was removed into a clean vial, and dried using anhydrous magnesium sulphate. The extract was filtered and concentrated under a gentle stream of nitrogen to a volume of either 50 or 100 μl. The *D. farinae* extract was fractionated by liquid chromatography over Florisil® (60-100 mesh, Aldrich Chemical Company, Gillingham, UK), using distilled hexane (100%), hexane: diethyl ether (5, 10, 20, 50%), diethyl ether (100%) and dichloromethane (100%) as eluants.

Collection of House Dust Mite Volatiles.

*Dermatophagoides pteronyssinus* mites were transferred from a Petri dish into the PTFE tube using a glass pipette tip and gentle suction. Silanized glass wool was compacted at both ends of the PTFE tube and attached to Tenax TA tubes, at one end, and sealed using Swagelok connectors at the other. A control was carried out simultaneously with another PTFE tube compacted with glass wool and either left empty or containing fish flakes. A positive humidified air-flow was introduced into the PTFE tubes at 100 ml/min, through a charcoal filter to reduce contamination, whilst a negative air-flow was drawn through the PTFE tubes simultaneously at 100 ml/min to indicate the air speed through the PTFE tubes. The air entrainment lasted for 24 h after which the Tenax TA tubes were removed.

Gas Chromatography (GC).

Mite extracts and chromatography fractions were analysed using a Hewlett Packard 6890 GC equipped with a cross-linked methyl silicone capillary column (50 m, 0.32 mm i.d, 0.52 μm film thickness) fitted with a cool-on-column injector and a flame ionization detector (FID). The GC oven was programmed to heat from 30° C. to 230° C. at 10° C./min, and held at 230° C. for 30 min. The carrier gas was hydrogen. Tenax TA samples were analysed on a Hewlett Packard 6890 GC machine, equipped with a cross-linked methyl silicone capillary column (50 m, 0.32 mm i.d, 0.82 μm film thickness) and a FID. Thermal desorption occurred inside the programmed temperature vaporisation unit (PTV), which was programmed to heat rapidly from 30° C. to 220° C. (16° C./sec). The GC oven was then maintained at 30° C. for 30 sec, and then programmed at 5° C./min increments to 120° C., followed by 10° C./min to 240° C. The carrier gas was hydrogen.

Gas Chromatography-Mass Spectrometry (GC-MS).

Mite extracts and fractions were analysed using a VG AutoSpec mass spectrometer (Fisons Instruments, Manchester, UK), coupled to a Hewlett Packard 5890 GC equipped with a cool-on-column injector. Ionization was by electron impact (70 eV, 250° C.). The GC oven was programmed to heat at 30° C. for 5 min and then 5° C./min until 250° C. The carrier gas was helium. Tentative identifications of mite-specific peaks were based upon comparison of acquired mass spectra with current MS databases (NIST, 2005) or with MS data published in the literature. Identifications were confirmed by peak enhancement with authentic samples (Pickett, 1990).

Confirmation of Limonene in *Dermatophagoides pteronyssinus* Extracts

Limonene was tentatively identified in *D. pteronyssinus* extracts by GC-MS but required confirmation using peak enhancement.

Materials and Methods

Equipment

R (+) Limonene 97% (Sigma Aldrich)
S (−) Limonene 98% (Sigma Aldrich)
*D. pteronyssinus* extract Procedure The racemic mixture of limonene was analyzed by GC on a β-cyclodextrin chiral capillary column (30 m×0.25 mm ID×0.25 μm film thickness) using a HP5890 GC (Agilent Technologies, UK) fitted with a cool-on-column injector and a FID. The GC oven temperature was maintained at 30° C. for 1 min after sample injection and then raised by 0.5° C./min to 40° C. where it was held for 20 min. The carrier gas was hydrogen.

Results

As shown in the graph in FIG. 1, R-(+)-limonene was the enantiomer present in the *D. pteronyssinus* extracts. R-(+)-Limonene was also found in extracts of the chicken mite, *Dermanyssus gallinae*.

R-(+)-Limonene was specific to *D. pteronyssinus* and identified in both solvent and air entrainment extracts, and was not identified in any *D. farinae* extracts.

EXAMPLE 4

Acaricides

Identification of Potential Acaricide to be Incorporated into Lure-and-Kill System Natural pyrethrum, known for its insecticidal properties, and azadirachtin, the active ingredient of neem, were tested for their lethal dosage (LD) using an established bioassay. Pyrethrum was more effective than azadirachtin, where little mortality was seen. Pyrethrum $LD_{50}$ values at 1, 2, 3 hours post exposure were 384.53 ppm, 20.829 ppm and 0.219 ppm, respectively (see FIG. 6). The $LD_{90}$ values for pyrethrum 2 and 3 hours post exposure were 2663.9 ppm and 225.86 ppm respectively.

REFERENCES

AKIYAMA, M., SAKATA, T., MORI, N., KATO, T., AMANO, H., and KUWAHARA, Y. 1997. Chemical ecology of astigmatid mites 0.46. Neryl formate, the alarm pheromone of *Rhizoglyphus setosus* Manson (Acarina: Acaridae) and the common pheromone component among four *Rhizoglyphus* mites. *Appl Entomol Zool* 32: 75-79.

ALLTECH ASSOCIATION, 1998. Quantitation methods in gas chromatography. www.alltechweb.com/productinfo/technical/edu/edu399.

ARLIAN, L. G., RAPP, C. M. and AHMED, S. G. 1990. Development of *Dermatophagoides pteronyssinus* (Acari, Pyroglyphidae). *J Med Entomol* 27: 1035-1040.

ARLIAN, L. G. 1992. Water-Balance and Humidity Requirements of House Dust Mites. *Exp Appl Acarol* 6: 15-35.

ARLIAN, L. G., NEAL, J. S., MORGAN, M. S., VYSZENSKI-MOHER, D. L., RAPP, C. M., and ALEXANDER, A. K. 2001. Reducing relative humidity is a practical way to control dust mites and their allergens in homes in temperate climates. *J Allergy Clin Immunol* 107: 99-104.

ARLIAN, L. G. and MORGAN, S. M. 2003. Biology, ecology, and prevalence of dust mites. *Immunol Allergy Clin* 23: 443+

BELLANTI, J. A., ZELIGS, B. J., MacDOWELL-CARNEIRO, A. L., ABACI, A. S., and GENUARDI. J. A. 2000. Study of the effects of vacuuming on the concentration of dust mite antigen and endotoxin. *Ann Allergy Asthma Immunol* 4: 249-254.

CALLAHAN, K. A., EGGLESTON, P. A., RAND, C. S., KANCHANARAKSA, S., SWARTZ, L. J., and WOOD, R. A. 2003. Knowledge and practice of dust mite control by specialty care. *Ann Allergy Asthma Immunol* 90: 302-307.

CAMERON, M. M. and HILL, N. 2002. Permethrin-impregnated mattress liners: a novel and effective intervention against house dust mites (Acari: Pyroglyphididae). *J Med Entomol* 39: 755-762.

CHANG, J. H., BECKER, A., FERGUSON, A., MANFREDA, J., SIMONS, E., CHAN, H., NOERTJOJO, K., and CHANYEUNG, M. 1996. Effect of application of benzyl benzoate on house dust mite allergen levels. *Ann Allergy Asthma Immunol* 77: 187-190.

COLLOFF, M. J. 1987. Effects of temperature and relative humidity on development times and mortality of eggs from laboratory and wild populations of the European house dust mite *Dermatophagoides pteronyssinus* (Acari, Pyroglyphidae). *Exp Appl Acarol* 3: 279-289.

COLLOFF, M. J. 1990. House Dust Mites-Part II Chemical control. *Pesticide Outlook* 1: 3-8

COLLOFF, M. J. 1991. Practical and theoretical aspects of the ecology of house dust mites (Acari: Pyroglyphidae) in relation to the study of mite mediated allergy. *Rev Med Vet Entomol* 79: 611-630.

COLLOFF, M. J., AYRES, J., CARSWELL, F., HOWARTH, P. H., MERRETT, T. G., MITCHELL, E. B., WALSHAW, M. J., WARNER, J. O., WARNER, J. A., and WOODCOCK, A. A. 1992. The control of allergens of dust mites and domestic pets—a position paper. *Clin Exp Allergy* 22: 1-28.

COLLOFF, M. J., TAYLOR, C., and MERRETT, T. G. 1995. The use of domestic steam cleaning for the control of house dust mites. *Clin Exp Allergy* 25: 1061-1066.

CROWTHER, D., WILKINSON, T., BIDDULPH, P., ORESZCZYN, T., PRETLOVE, S., and RIDLEY, I. 2006. A simple model for predicting the effect of hygrothermal conditions on populations of house dust mite *Dermatophagoides pteronyssinus* (Acari: Pyroglyphidae). *Exp Appl Acarol* 39: 127-148.

CUSTOVIC, A. and CHAPMAN, M. 1998. Risk levels for mite allergens. Are they meaningful? *Allergy* 53: 71-76.

CUSTOVIC, A., FLETCHER, A., PICKERING, C. A. C., FRANCIS, H. C., GREEN, R., SMITH, A., CHAPMAN, M., and WOODCOCK, A. 1998. Domestic allergens in public places III: house dust mite, cat, dog and cockroach allergens in British hospitals. *Clin Exp Allergy* 28: 53-59.

de BOER, R. 1998. Reflections on the control of mites and mite allergens. *Allergy* 53: 41-46.

de BOER, R. 2003. The effect of sub-floor heating on house-dust-mite populations on floors and in furniture. *Exp Appl Acarol* 29: 315-330.

FAIN, A. and HART, B. J. 1986. A new simple technique for extraction of mites, using the difference in density between ethanol and saturated NaCl (Preliminary Note). *Acarologia* 27: 255-256.

FAIN, A., GUERIN, B., and HART, B. J. 1990. Mites and Allergic Disease. Allerbio, France.

FOWLER, J., COHEN, L., and JARVIS, P. 1998. Practical statistics for field biology. John Wiley & Sons, Chichester.

FRANZ, J., SCHULTZ, S., FUHLENDORFF, J., WEGENER, R., MASUCH, G., BERGMANN, K., and MUSKEN, H. 2001. Language of astigmatic mites: Pheromones—an evaluation from a biological viewpoint, European Association of Acarologists 5th Symposium., Berlin.

GLASS, E. V., YODER, J. A., and NEEDHAM, G. R. 1998. Clustering reduces water loss by adult American house dust mites *Dermatophagoides farinae* (Acari: Pyroglyphidae). *Exp Appl Acarol* 22: 31-37.

GLASS, E. V., YODER, J. A., and NEEDHAM, G. R. 2001. Evaluation of possible arrestant-aggregation pheromones in the American House Dust Mite, *Dermatophagoides farinae* Hughes (Astigmata: Pyroglyphidae). *Int J Acarol* 27: 63-66.

HART, B. J. and Fain, A. 1987. A new technique for isolation of mites exploiting the difference in density between ethanol and saturated NaCl-qualitative and quantitative studies. *Acarologia* 28: 251-254.

HART, B. J. 1995. The biology of allergenic domestic mites—an update. *Clin Rev Allergy Immunol* 13: 115-133.

HEIDE, S., KAUFFMAN, H. F., DUBOIS, A., and MONCHY, J. 1997. Allergen-avoidance measures in homes of house dust mite allergic asthmatic patients: effects of acaricides and mattress encasings. *Allergy* 52: 921-927.

HILL, N., and CAMERON, M. M. (1999). A novel method to compare house dust mite allergen removal and retention by different vacuum cleaners, pp. 644, *Proceedings of the 3rd International Conference on Urban Pests*, Czech University of Agriculture, Prague, Czech.

ISSAC. 1998. Worldwide variation in prevalence of symptoms of asthma, allergic rhinoconjunctivitis, and atopic eczema. *Lancet* 351: 1225-32.

JACKSON, A. P., FOSTER, A. P., HART, B. J., HELPS, C. R., and SHAW, S. E. 2005. Prevalence of house dust mites and *Dermatophagoides* group 1 antigens collected from bedding, skin and hair coat of dogs in south-west England. *Vet Dermatol* 16: 32-38.

KUWAHARA, Y., LEAL, W. S., and SUZUKI, T. 1990. Pheromone study on astigmatid mites XXVI. Comparison of volatile components between *Dermatophagoides farinae* and *D. pteronyssinus* (Astigmata, Pyroglyphidae). *Jpn J Sanit Zool* 41: 23-28.

KUWAHARA, Y., MATSUMOTO, K., WADA, Y., and SUZUKI, T. 1991. Chemical ecology on astigmatid Mites. XXIX. Aggregation pheromone and kairomone activity of synthetic lardolure (1R,3R,5R,7R)-1,3,5,7-tetramethyldecyl formate and its optical isomers to *Lardoglyphus konoi* and *Carpoglyphus lactis* (Acari: Astigmata) *Appl Ent Zool* 26: 85-89

KUWAHARA, Y. 1997. Volatile compounds produced by two species of *Dermatophagoides* mites. *Skin Res* 39: 52-55.

KUWAHARA, Y. 2004. Chemical ecology of astigmatid mites. In R. Carde and J. G. Millar [eds.], Advances in Insect Chemical Ecology. Cambridge University Press, Cambridge.

KUWAHARA, Y. 2006. How mites (Astigmata) control the emission of three types of pheromones from the same gland, depending upon environmental cues and the functional characteristics of active compounds. ABSTRACT. $12^{th}$ International Congress of Acarology, Amsterdam, 2006.

LUCZYNSKA, C., KARLA ARRUDA, L., PLATTS-MILLS, T. A. E., MILLER, J., LOPEZ, M., and CHAPMAN, M. 1989. A two-site monoclonal antibody ELISA for the quantification of the major *Dermatophagoides* spp. allergens, Der p 1 and Der f 1. *J Immunol Meth* 118: 227-235.

LUCZYNSKA, C., TREDWELL, T., SMEETON, N., and BURNEY, P. 2003. A randomized controlled trial of mite allergen-impermeable bed covers in adult mite-sensitized asthmatics. *Clin Exp Allergy* 33: 1648-1653

McDONALD, L. G. and TOVEY, E. R. 1992. The role of water temperature and laundry procedures in reducing house dust mite populations and allergen content of bedding. *J Allergy Clin Immunol* 90: 599-608.

NAGAKURA, T., YASUEDA, H., OBATA, T., KANMURI, M., MASAKI, T., IHARA, N., and MAEKAWA, K. 1996.

Major *Dermatophagoides* mite allergen, Der 1, in soft toys. *Clin Exp Allergy* 26: 585-589.

NIST, 2002. Standard Referece Data Base (Version 3.0.1). Gaithersburg, Md.

ORIBE, Y. and MIYAZAKI, Y. 2000. Effects of relative humidity on the population growth of house dust mites. *J Physiol Anthropol Appl Hum Sci* 19: 201-203.

PLATTS-MILLS, T. A. E., WARD, G. W. SPORIK, R., GELBER, L. E., CHAPMAN, M., and. HEYMANN, P. W. 1991. Epidemiology of the relationship between exposure to indoor allergens and asthma. *Int Arch Allergy Appl Immunol* 94: 339-345.

REKA, S., SUTO, C., and YAMAGUCHI, M. 1992. Evidence of aggregation pheromone in the faeces of house dust mite *Dermatophagoides farinae. Jpn J Sanit Zool* 43: 339-341.

ROBINSON, C., KALSHEKER, N. A., SRINIVASAN, N., KING, C. M., GARROD, D. R., THOMPSON, P. J., and STEWART, G. A. 1997. On the potential significance of the enzymatic activity of mite allergens to immunogenicity. Clues to structure and function revealed by molecular characterization. *Clin Exp Allergy* 27: 10-21.

SKELTON, A. C., BIRKETT, M. A., PICKETT, J. A., and CAMERON, M. M 2007. Olfactory responses of medically and economically important mites (Acari: Pyroglyphidae and Acaridae) to volatile chemicals. *J Med Entomol* 44 (2) 367-371

SHIMIZU, N., MORI, N., and KUWAHARA, Y. 2001. Aggregation pheromone activity of the female sex pheromone, β-acaridial, in *Caloglyphus polyphyllae* (Acari: Acaridae). *Biosci Biotechnol Biochem* 65: 1724-1728.

SPIEKSMA, F. T. M. 1967. The house dust mite *Dermatophagoides pteronyssinus* (Trouessart, 1897) producer of the house dust allergen (Acari: Psoroptidae). PhD thesis. Leiden N. V. Drukkerij. Battelje & Terpstra, Leiden.

TATAMI, K., MORI, N., NISHIDA, R., and KUWAHARA, Y. 2001. 2-Hydroxy-6-methylbenzaldehyde: the female sex pheromone of the house dust mite *Dermatophagoides farinae* (Astigmata: Pyroglyphidae). *Med Entomol Zool* 52: 279-286.

THIND, B. 2005. A new versatile and robust mite trap for detection and monitoring of storage mites in cereal and allied industries. *Exp Appl Acarol* 35: 1-15.

TREEHORST, I., HAK, E., OOSTUBF, A. J., TEMPELS-PAVLICA, Z., dE MONCHY, J. G. R., BRUIJNZEEL-KOOMEN, C. A., AALBERSE, R. C., and GERTH van WIJK, R. 2003 Evaluation of impermeable covers for bedding in patients with allergic rhinitis. *New Eng J Med* 349: 237-246

TOVEY, E., CHAPMAN, M., and PLATTS-MILLS, T. A. E. 1981. Mite faeces are a major source of house dust allergens. *Nature* 289: 592-593.

UEHARA, K., TOYODA, Y., and KONISHI, E. 2000. Contamination of passenger trains with *Dermatophagoides* (Acari: Pyroglyphidae) mite antigen in Japan. *Exp Appl Acarol* 24: 727-734.

van den BEMT, L., van KNAPEN, L., de VRIES, M. P., JANSEN, M., CLOOSTERMAN, S., van SCHAYCK, C. P. 2004. Clinical effectiveness of a mite allergen-impermeable bed-covering system in asthmatic mite-sensitive patients. *J Allergy Clin Immunol* 114: 858-862.

VOORHORST, R., SPIEKSMA, M. I. A., and SPIEKSMA, F. T. M. 1964. Is a mite (*Dermatophagoides* sp.) the producer of the house-dust allergen? *Allergie and Asthma* 10: 329-334.

WHO, 2006. Bronchial asthma. Fact sheet No 206. www.who.int/mediacentre/factsheets/fs206/en/print.html.

YODER, J. A., DENLINGER, D. L., and WOLDA, H. 1992. Aggregation promotes water conservation during diapause in the tropical fungus beetle, *Stenotarsus rotundus. Entomol Exp Appl* 63: 203-205.

The invention claimed is:

1. A composition, comprising at least 0.01% neryl formate and pyrethrum, wherein the composition is in powder form or forms a powder on drying.

2. The composition according to claim 1, comprising one or more additional attractants.

3. The composition of claim 1, wherein the composition comprises at least 0.05% neryl formate.

4. The composition of claim 1, wherein the composition comprises at least 0.1% neryl formate.

5. The composition of claim 1, wherein the composition is present in silicate particles.

6. The composition according to claim 1, further comprising limonene.

7. A composition, comprising at least 0.01% neryl formate and pyrethrum, wherein the composition is in powder form.

8. The composition of claim 7, wherein the composition comprises 0.05% neryl formate.

9. A method of luring and killing house dust mites of the species *Dermatophagoides farinae* or *D. pteronyssinus*, comprising:
    luring the house dust mites using at least 0.01% powdered neryl formate; and
    exposing the house dust mites to an acaricide, thereby luring and killing the house dust mites.

10. The method of claim 9, comprising luring the house dust mites with at least 0.05% powdered neryl formate.

11. The method of claim 9, comprising luring the house dust mites with at least 0.5% powdered neryl formate.

12. The method of claim 9, comprising luring the house dust mites with at least 0.1% powdered neryl formate.

13. The method of claim 9, wherein the neryl formate is placed within 5 cm of the house dust mites.

14. The method of claim 9, wherein the neryl formate is placed within 3 cm of the house dust mites.

15. The method of claim 9, wherein the house dust mites are lured by the neryl formate for 20 minutes.

16. The method of claim 9, wherein the acaricide is pyrethrum.

17. A composition, comprising 10 ng or 100 ng of neryl formate and an acaricide compound that is toxic to the house dust mites, wherein the composition is in powder form or forms a powder on drying.

* * * * *